United States Patent
Wang et al.

(10) Patent No.: US 11,787,721 B2
(45) Date of Patent: Oct. 17, 2023

(54) TAILINGS SETTLING-DEWATERING-SOLIDIFYING DEVICE AND EXPERIMENTAL METHOD THEREOF

(71) Applicant: Kunming University of Science and Technology, Kunming (CN)

(72) Inventors: Guangjin Wang, Kunming (CN); Chengliang Zhang, Kunming (CN); Xiangyun Kong, Kunming (CN); Mingyu He, Kunming (CN)

(73) Assignee: Kunming University of Science and Technology, Kunming (CN)

( * ) Notice: Subject to any disclaimer, the term of this patent is extended or adjusted under 35 U.S.C. 154(b) by 191 days.

(21) Appl. No.: 17/349,029

(22) Filed: Jun. 16, 2021

(65) Prior Publication Data

US 2022/0324739 A1    Oct. 13, 2022

(30) Foreign Application Priority Data

Apr. 12, 2021    (CN) .......................... 202110388137.9
Apr. 12, 2021    (CN) .......................... 202120733925.2

(51) Int. Cl.
*C02F 11/14*    (2019.01)
*C02F 11/122*   (2019.01)
(Continued)

(52) U.S. Cl.
CPC .............. *C02F 11/14* (2013.01); *B01D 21/01* (2013.01); *B01D 21/08* (2013.01); *B01D 21/302* (2013.01);
(Continued)

(58) Field of Classification Search
None
See application file for complete search history.

(56) References Cited

FOREIGN PATENT DOCUMENTS

CN    109100284 A  * 12/2018  ......... G01N 15/0826
CN    109580922 A  *  4/2019  ............. G01N 33/42

OTHER PUBLICATIONS

Chen, X.; Jin, X.; Jiao, H.; Yang, Y.; Liu, J. Pore Connectivity and Dewatering Mechanism of Tailings Bed in Raking Deep-Cone Thickener Process. Minerals 2020, 10, 375. https://doi.org/10.3390/min10040375 (Year: 2020).*

* cited by examiner

*Primary Examiner* — Bradley R Spies
*Assistant Examiner* — Jeannie Mcdermott
(74) *Attorney, Agent, or Firm* — Georgi Korobanov

(57) ABSTRACT

The invention relates to a tailings settling-dewatering-solidifying device and an experimental method thereof, which falls into the technical field of mine engineering and mine geotechnical engineering, comprising a tailings settling device including a water tank, charging barrels I and II, and a reaction tank made of a transparent material, a dewatering device including an intelligent type controller, a circular base, a gas cylinder, a permeable stone, a piston, a metal rod and a water return barrel, a solidifying device including a charging barrel III and a tailings barrel, a stirring system including a stirrer, a rotary shaft and an electric motor, a dynamic real-time monitoring system including a high-definition electronic camera and a computer, and a three-layer framework. Through integration of tailings settling-dewatering-solidifying, the device can effectively improve tailings treatment efficiency, facilitate data collection and analysis, adjust medicament concentration in real time, meet enterprises' requirements, and reduce enterprise cost.

9 Claims, 9 Drawing Sheets

(51) Int. Cl.
*C02F 1/00* (2023.01)
*B01D 21/01* (2006.01)
*B01D 21/30* (2006.01)
*B01D 21/08* (2006.01)
*G01N 33/24* (2006.01)
*B01D 21/32* (2006.01)
*C02F 103/10* (2006.01)

(52) U.S. Cl.
CPC .............. *B01D 21/32* (2013.01); *C02F 1/008* (2013.01); *C02F 11/122* (2013.01); *G01N 33/24* (2013.01); *C02F 2103/10* (2013.01); *C02F 2209/005* (2013.01); *C02F 2209/40* (2013.01)

TAILINGS SETTLING-DEWATERING-SOLIDIFYING DEVICE AND EXPERIMENTAL METHOD THEREOF

CROSS REFERENCE TO RELATED APPLICATION

The invention relates to a tailings settling-dewatering-solidifying device and an experimental method thereof, and belongs to the technical field of mining engineering and mine geotechnical engineering.

BACKGROUND OF THE INVENTION

Tailings are discharged waste obtained after grinding ores and selecting useful components. With the advancement of mineral resource development technology in China, the tailings stacked at a tailings dam are grinded to be smaller and smaller when the mineral processing process is improved and the tailings filling technology is applied on a large scale; compared with conventional tailings, the superfine tailings are featured by great specific surface area and small particle granularity. At present, the tailings with granularity smaller than 53 um are relatively common, but the products of some concentration plants have granularity of −30 um along with popularization of superfine ore grinding equipment and the separation technology, which bring serious hidden danger to the safety of the tailings dam. The tailings discharged from a dressing mill generally have a concentration of about 25%-35%, which is far lower than the requirements of the tailings dam; and the low-concentration tailings slurry is generally subjected to processes such as flocculating settling, dense dewatering and tailings solidifying to form high-concentration tailings slurry or a tailings filter cake which can be discharged into a tailings pond or can be filled underground.

The processes of flocculating settling, dense dewatering and tailings solidifying have different influence factors which may affect final filling or stacking. For the current mining industry, there is no device integrating the three processes.

SUMMARY OF THE INVENTION

To overcome the problems and the defects in the prior art, the invention provides a tailings settling-dewatering-solidifying device and an experimental method thereof, which can be used for a flocculating-dehydrating-settling experiment in a laboratory, simplifies the process flow by obtaining the optimal value of the influence factors at each experimental stage, and reduces the process cost. The invention is realized by the following technical solution.

The invention provides the following technical solution: a tailings settling-dewatering-solidifying device includes a tailings settling device, a dewatering device, a solidifying device, a stirring system, a dynamic real-time monitoring system and a three-layer framework 25;

the tailings settling device includes a water tank 1, a charging barrel I 10, a charging barrel II 35 and a reaction tank 44 which is made of a transparent material;

the dewatering device includes an intelligent controller 39, a circular base 14, a gas cylinder 15, a permeable stone 18, a piston 17, a metal rod 16 and a water return barrel 50;

the solidifying device includes a charging barrel III 23 and a tailings barrel 52; the stirring system includes a stirrer 47, a rotary shaft 48 and an electric motor 53;

the dynamic real-time monitoring system includes a high-definition electronic camera 21 and a computer 28;

the charging barrel I 10 and the charging barrel II 35 are placed on a second-layer plate of the three-layer framework 25, and the charging barrel III 23, the reaction tank 44 and the water return barrel 50 are placed on a bottom-layer plate of the three-layer framework 25; a pipeline hole is formed in the framework at each layer; a water inlet 29 is formed in the upper end of the water tank 1 and a water outlet 33 is formed in the lower end of the water tank 1, the left side of the water tank 1 is connected to a water inlet end of a three-phase pipeline joint 6 through a pipeline 5; a horizontal water outlet end of the three-phase pipeline joint 6 is connected to the horizontal end of a right-angled pipeline joint I 4 through a pipeline 5, the vertical water outlet end of the three-phase pipeline joint 6 passes through the uppermost-layer plate of the three-layer framework 25 through the pipeline 5 and then is connected to a charging barrel cap I 9 at the upper end of the charging barrel I 10; the right side of the water tank 1 is connected to the horizontal end of the right-angled pipeline joint II 31 through a pipeline 5, and the vertical end of the right-angled pipeline joint II 31 passes through the uppermost-layer plate of the three-layer framework 25 through a pipeline 5 and then is connected to a charging barrel cap II 34 at the upper end of the charging barrel II 35; the vertical end of the right-angled pipeline joint I 4 sequentially passes through the uppermost-layer plate and the middle-layer plate of the three-layer framework 25 through a pipeline 5 and then is connected to a charging barrel cap III 22 at the upper end of the charging barrel III 23; a control switch I 2 and a flowmeter I 7 are arranged on the pipeline 5 between the water tank 1 and the three-phase pipeline joint 6; a control switch II 3 is arranged on the pipeline 5 between the three-phase pipeline joint 6 and the right-angled pipeline joint 14; a control switch IV 8 is arranged on the pipeline 5 between the three-phase pipeline joint 6 and the charging barrel cap I 9; a control switch III 30 and a flowmeter II 32 are arranged on the pipeline 5 between the water tank 1 and the right-angled pipeline joint II 31; the water outlet end on the bottom of the charging barrel III 23 is connected to one side of the bottom of the reaction tank 44 through a pipeline 5; a control switch VIII 24 is arranged on the pipeline 5 between the charging barrel III 23 and the reaction tank 44; one side of the middle part of the reaction tank 44 is connected to one end of the first water outlet pipeline, and the other end of the first water outlet pipeline extends into the water return barrel 50; a control switch VII 45 is arranged on the first water outlet pipeline; the bottom of the reaction tank 44 is connected to one end of the second water outlet pipeline, and the other end of the second water outlet pipeline extends into the tailings barrel 52, and a control switch IX 51 is arranged on the second water outlet pipeline; the bottom of one side of the charging barrel I 10 passes through the middle-layer plate of the three-layer framework 25 through a pipeline 5 and then communicates with the upper end of one side of the reaction tank 44; a control switch V 11 and a flowmeter IIII 12 are arranged on the pipeline 5 between the charging barrel I 10 and the reaction tank 44; the bottom of one side of the charging barrel II 35 passes through the middle-layer plate of the three-layer framework 25 through pipeline 5 and then communicates with the upper end of the other side of the reaction tank 44; a control switch VI 36 and a flowmeter IV 38 are arranged on the pipeline 5 between the charging barrel II 35 and the reaction tank 44; a circular base 14 is fixedly arranged at the lower side of the second-layer plate of the framework 25; the lower end of the circular base 14 is connected to a gas cylinder 15; the gas cylinder 15 is connected to the intelligent controller 39 through an electric wire; the piston 17 is arranged on the top of the rection tank 44; the permeable stone 18 is arranged inside the piston 17; the metal rod 16 is arranged on the upper part of the piston 17; the stirrer 47 is mounted inside the reaction tank 44; a rotary shaft 48 of the stirrer 47 is rotatably connected to the inner wall of the reaction tank 44 through a tube wall interface 49; the rotary shaft 48 is connected to the electric motor 53 through an electric wire; a reversed pipeline hole 19 is formed in the upper-end side wall of the reaction tank 44; and the high-definition electronic camera 21 is mounted on the position opposite to the reaction tank 44 and is connected to the computer 28 through an electric wire.

Preferably, wheels 27 with brake valves 26 thereon are arranged on the bottom of the three-layer framework 25.

Preferably, the intelligent controller 39 is fixedly arranged at the front side of the second-layer plate of the three-layer framework 25.

Preferably, the charging barrel cap I 9 is rotatably connected to the pipeline 5 at the upper end through threads, and the lower part of the charging barrel cap I 9 is rotatably connected to the charging barrel I 10 through threads; the charging barrel I 10 is connected to the pipeline 5 on the bottom through threads; and a connecting way between the charging barrel II 35 and the charging barrel III 23 is the same as the charging barrel I 10.

Preferably, the piston 17 includes two rubber stoppers with big and small apertures, which are connected through a rubber band; and the diameters of the permeable stone 18 and the metal rod 16 are slightly smaller than the apertures of the two rubber stoppers of the piston 17.

Preferably, the water inlet 29 and the water outlet 33 are opened or closed by the rubber stoppers.

Preferably, a display control screen 40, a mode selecting key 41 and a switch button 42 are arranged on the intelligent controller 39.

Preferably, the circular base 14 is fixed to the lower side of the second-layer plate of the framework 25 through a screw 55, and the circular base 14 is welded and fused with the gas cylinder 15 through metal; and the intelligent controller 39 is fixed at the front side of the second-layer plate of the framework 25 through an electric adhesive tape.

An experimental method of the tailings settling-dewatering-solidifying device includes the following steps:

before the experiment, filling a flocculant a and a flocculant b into the charging barrel I 10 and the charging barrel II 35, injecting low-concentration fine-grained tailings slurry into the reaction tank 44 through the reserved pipeline hole 19, and filling a solidifying agent into the charging barrel III 23;

when the experiment starts, opening the water inlet 29 and closing the water outlet 33 to fill up the water tank 1 with water, opening the control switch I 2, the control switch III 30 and the control switch IV 8 while closing the control switch II 3, the control switch V 11 and the control switch VI 36, controlling the water flow rate by adjusting the opening and closing degree of the control switch I 2 and the control switch III 30, monitoring the water flow rate by the flowmeter I 7 and the flowmeter II 32, making water flow into the charging barrel I 10 and the charging barrel II 35 through corresponding pipelines 5, mixing the water flow with different flow rates with the flocculants a and b to obtain different flocculant concentrations; after obtaining the water flow needed for the experiment, closing the control switch I 2, the control switch IV 8 and the control switch III 30 until the water flows into the corresponding charging barrels;

after mixing the water with the flocculants a and b in the charging barrel I 10 and the charging barrel II 35, opening the control switch V 11, controlling the flow rate of the flocculant a by adjusting the opening and closing degree of the control switch V 11, monitoring the flow rate of the flocculant a by the flowmeter III 12, and closing the control switch V 11 after the flocculant a with a set flow rate flows into the reaction tank 44; switching on an electric motor switch 54 of the electric motor 53, making the stirrer 47 start working, switching off the electric motor switch 54 of the electric motor 53 after stirring for 10 minutes, and making the stirrer 47 stop working; switching on the control switch VI 36, controlling the flow rate of the flocculant b by adjusting the opening and closing degree of the control switch VI 36, monitoring the flow rate of the flocculant b by the flowmeter IV 38, and switching off the control switch VI 36 after the flocculant with the set flow rate flows into the reaction tank 44; making the flocculants a and b have settling reaction with low-concentration fine-grained tailings slurry in the reaction tank 44, photographing a reaction process through the high-definition electronic camera 21, transmitting pictures into the computer 28 for data processing, and basically accomplishing the settling reaction while the data not changed anymore;

after settling reaction is completed, making the experiment enter a dewatering process: electrifying the intelligent controller 39 by an external power supply, switching on the switch button 42 on the intelligent controller 39, making the gas cylinder 15 start working, pushing the metal rod 16 to move downwards by the gas cylinder 15, driving the piston 17 to move downwards by the metal rod 16, separating water from the tailings by the permeable stone 18 mounted in the piston 17 in a downward moving process, switching off the switch button 42 of the intelligent controller 39 while the piston 17 moves to the lower side of the control switch VII 45, making the gas cylinder 15 stop working, standing for certain time, switching on the control switch VII 45 while the water level on the upper part of the permeable stone does not rise again, making upper water flow into the water return barrel 50 through the pipeline 5, switching off the control switch VII 45 after water is completely drained, holding the metal rod 16 with hands, lifting the piston to the top of the reaction tank 44 until the dewatering process is basically accomplished;

after the dewatering process is accomplished, entering a solidifying reaction stage: switching on the control switch I 2 and the control switch II 3, switching off the control switch IV 8, controlling the water flow rate by adjusting the opening and closing degree of the control switch I 2, monitoring in real time by the flow rate meter I 7, making certain amount of water flow into the charging barrel III 23 through the pipeline 5, mixing the water with a solidifying agent in the charging barrel III 23, switching on the control switch VIII 24, making the solidifying agent with certain concentration flow into the reaction tank 44, and switching off the control switch VIII 24 after mixing the solidifying agent with the dewatered fine-grained tailings slurry; switching on the electric motor switch 54 of the electric motor 53, making the stirrer 47 start working, switching off the electric motor switch 54 of the electric motor 53 after stirring for set time, and making the stirrer 47 stop working; and switching on the control switch IX 51, and making the solidified tailings flow into a tailings barrel 52 until the whole experiment is accomplished.

The invention has the following beneficial effects:

1. The device can be used for performing a tailings settling-dewatering-solidifying test in a laboratory.

2. The device adopts the gas cylinder to push the metal rod to move downwards and can realize integrally moving downwards for separating water from the tailings through the permeable stone, where the metal rod is connected to the piston, and the piston is connected to the permeable stone.

3. The stirrer used by the device can effectively realize dual purposes, can be applied to the tailings settling and solidifying reaction process well, and reduces the cost of the enterprises.

4. The reaction tank of the device is made of a transparent material, and the reaction picture at each reaction stage can be continuously taken through the high-definition electronic camera 21; and the data are transmitted to the computer for data analysis after the test to obtain the results.

5. The device is based on a practical project for combining settling, dewatering and solidifying processes of the tailings, which are accomplished in one reaction process, so that investment cost of the enterprises can be greatly reduced while work efficiency is improved.

In the figures: 1, water tank; 2, control switch I; 3, control switch II; 4, right-angled pipeline joint I; 5, pipeline; 6, three-phase pipeline joint; 7, flowmeter I; 8, control switch IV; 9, charging barrel cap I; 10, charging barrel I; 11, control switch V; 12, flowmeter III; 13, right-angled pipeline joint III; 14, circular base; 15, gas cylinder; 16, metal rod; 17, piston; 18, permeable stone; 19, reserved pipeline hole; 20, right-angled pipeline joint IV; 21, high-definition electronic camera; 22, charging barrel cap III; 23, charging barrel III; 24, control switch VIII; 25, framework; 26, brake valve; 27, wheel; 28, computer; 29, water inlet; 30, control switch III; 31, right-angled pipeline joint II; 32, flowmeter II; 33, water outlet; 34, charging barrel cap II; 35, charging barrel II; 36, control switch IV; 37, right-angled pipeline joint V; 38, flowmeter IV; 39, intelligent controller; 40, display control screen; 41, mode selector; 42, switch button; 43, right-angled pipeline joint VI; 44, reaction tank; 45, control switch VII; 46, right-angled pipeline joint VII; 47, stirrer; 48, rotary shaft; 49, tube wall interface; 50, water return barrel; 51, control switch IX; 52, tailings barrel 53, electric motor; 54, electric motor switch; and 55, screw.

DETAILED DESCRIPTION OF THE PREFERRED EMBODIMENTS

The invention is further explained in combination with the drawings and specific embodiments.

Figure 1:
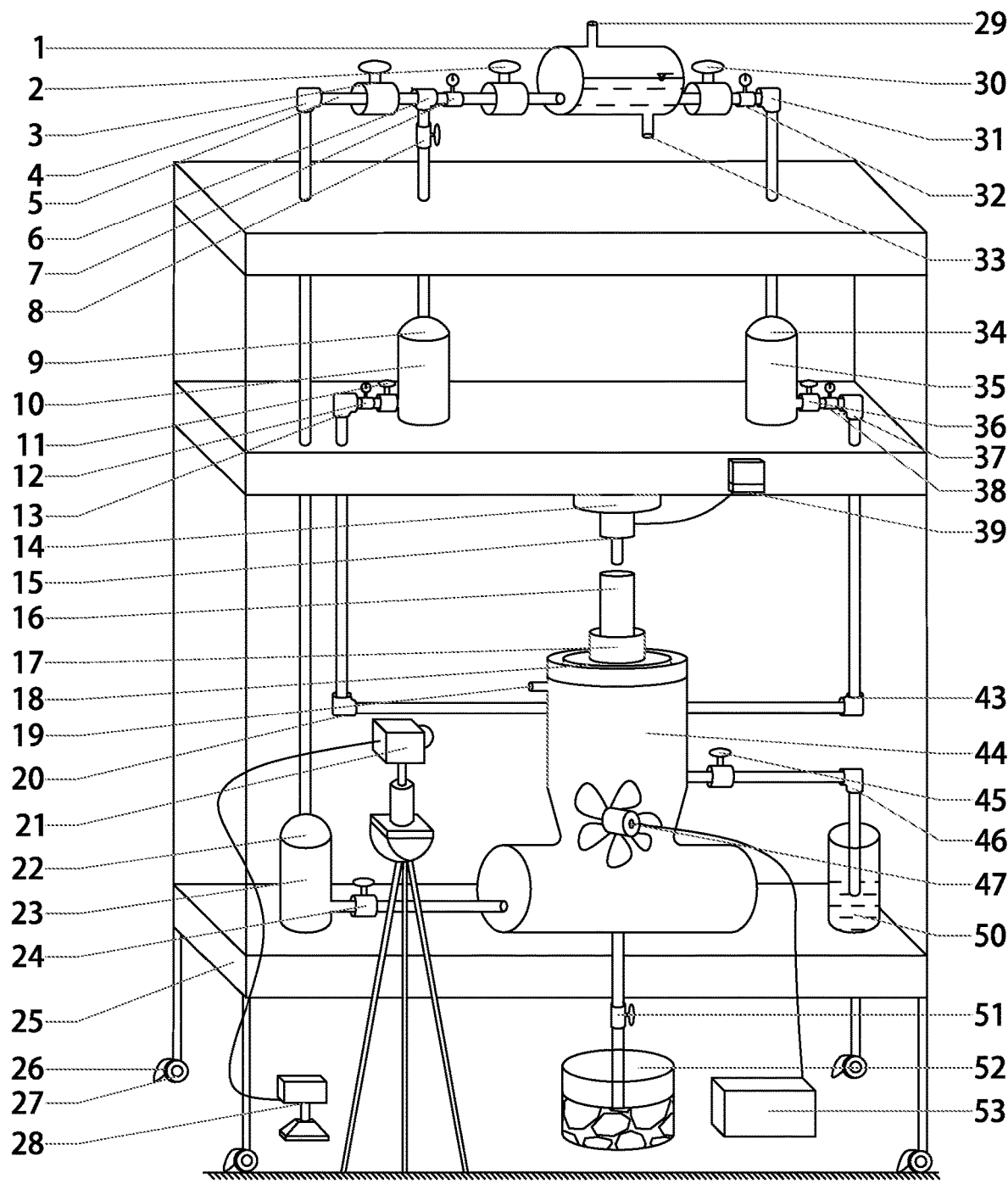
FIG. 1 is a schematic diagram showing the planar structure of the invention.
Figure 2:
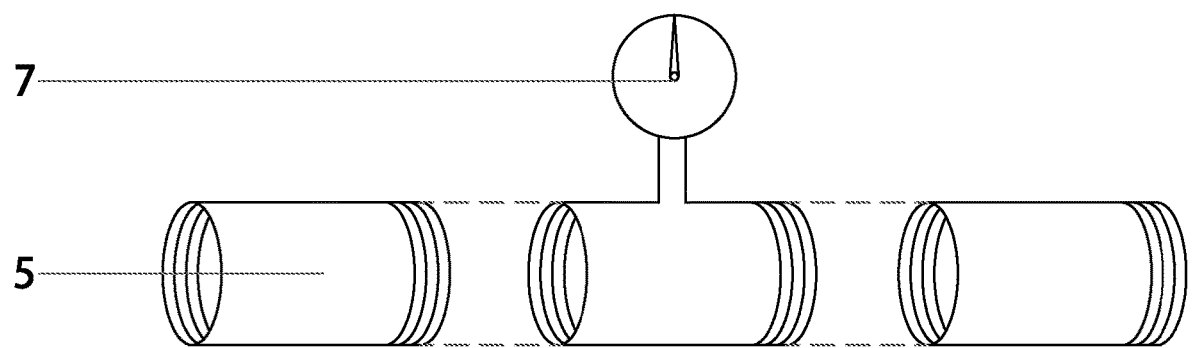
FIG. 2 is a schematic diagram showing connection between the flowmeter and the pipeline.
Figure 3:
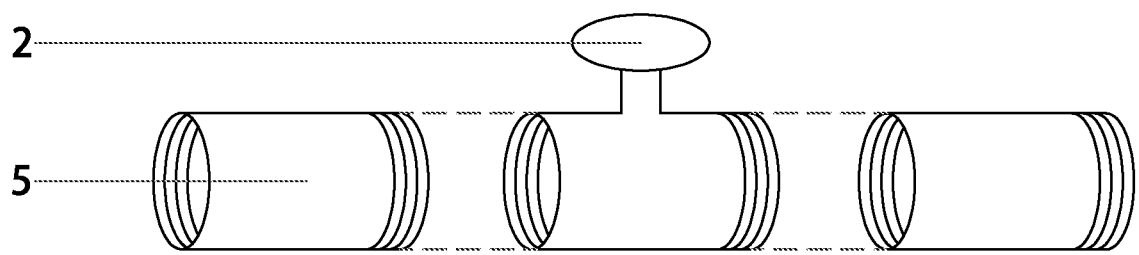
FIG. 3 is a schematic diagram showing connection between the control switch and the pipeline.
Figure 4:
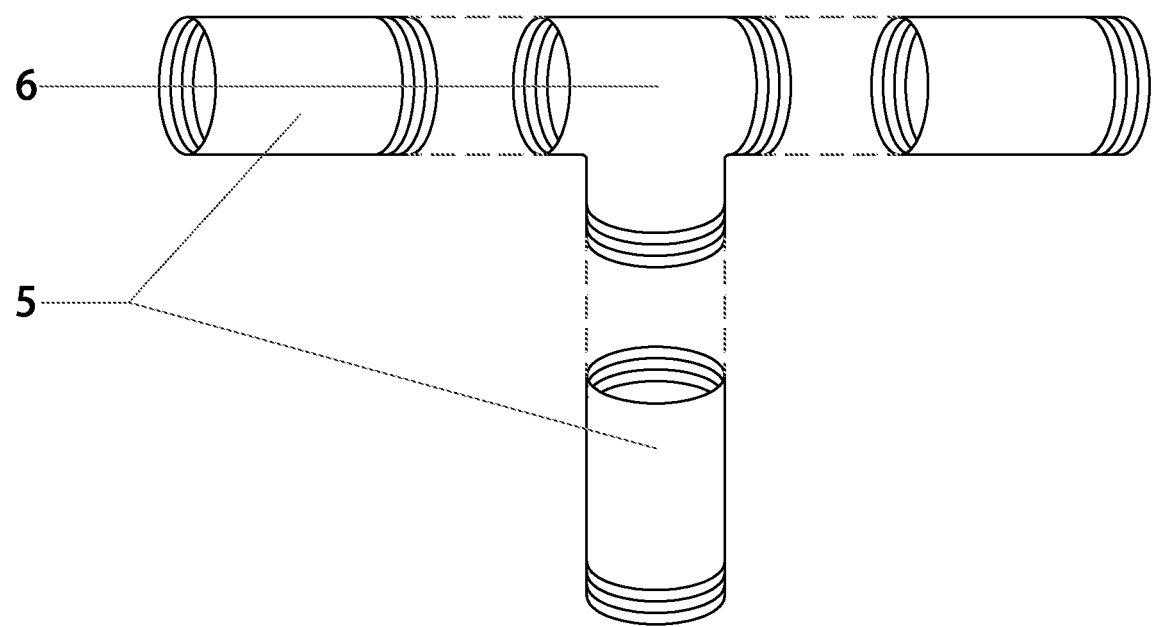
FIG. 4 is a schematic diagram showing connection between the three-phase pipeline interface and the pipeline.
Figure 5:
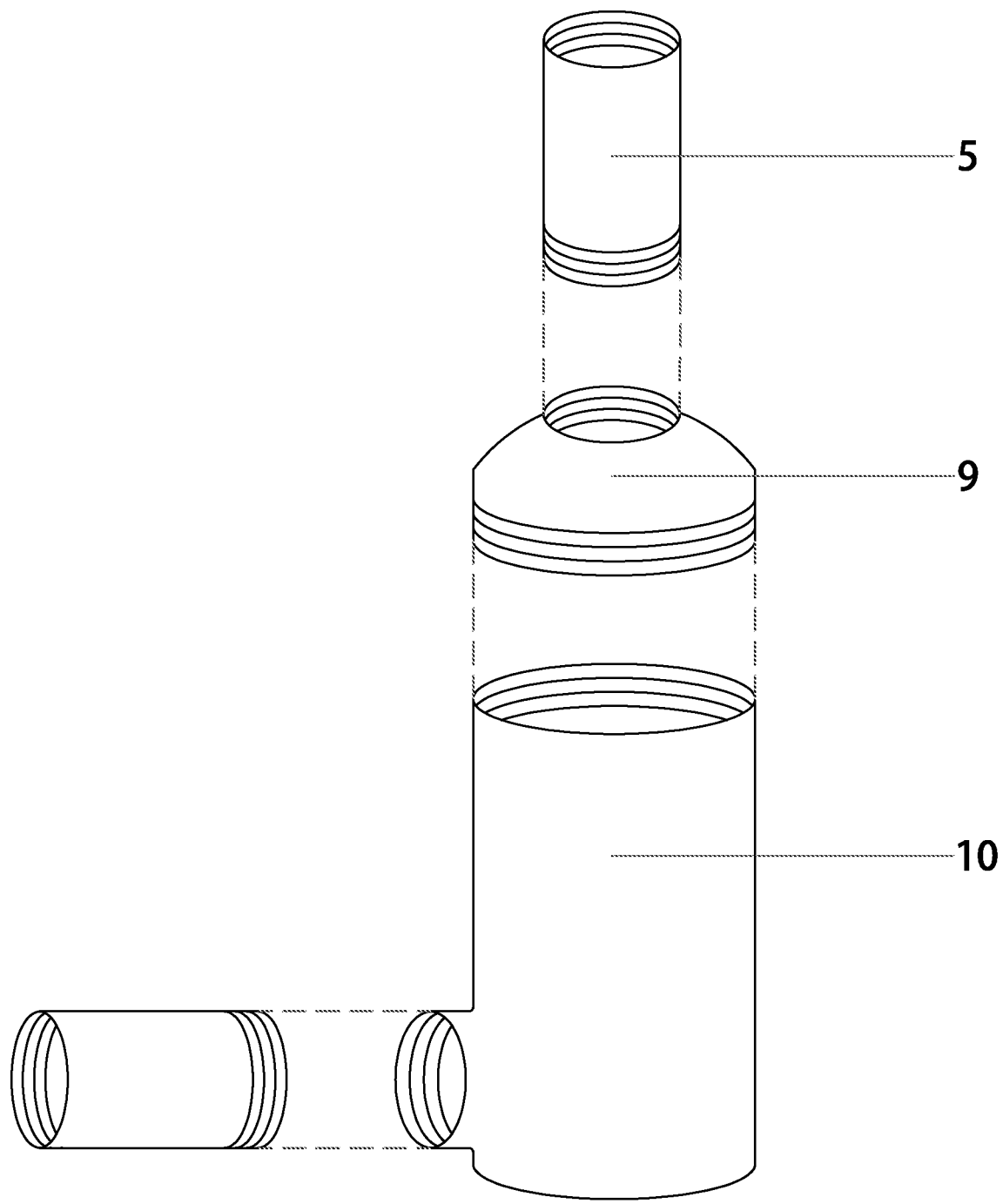
FIG. 5 is a schematic diagram showing connection among the pipeline, the charging barrel cap and the charging barrel.
Figure 6:
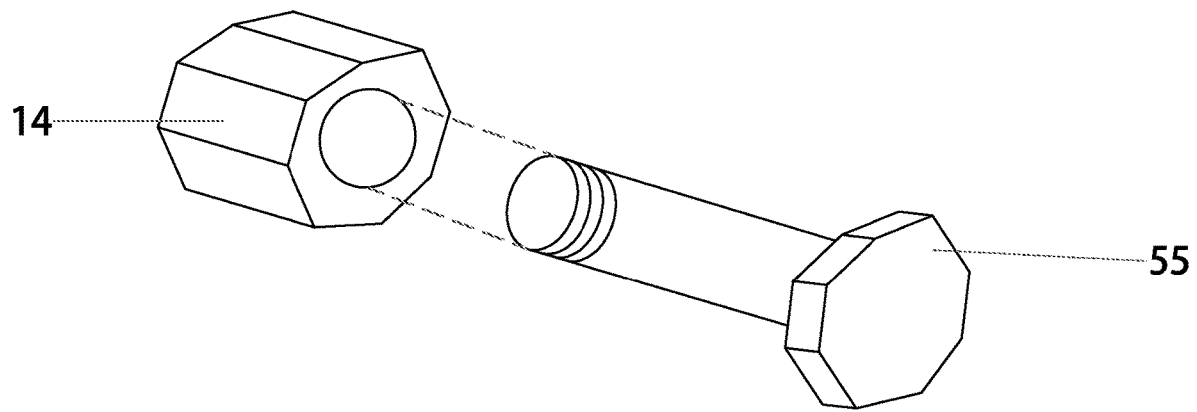
FIG. 6 is a schematic diagram showing connection between the circular base and the framework.
Figure 7:
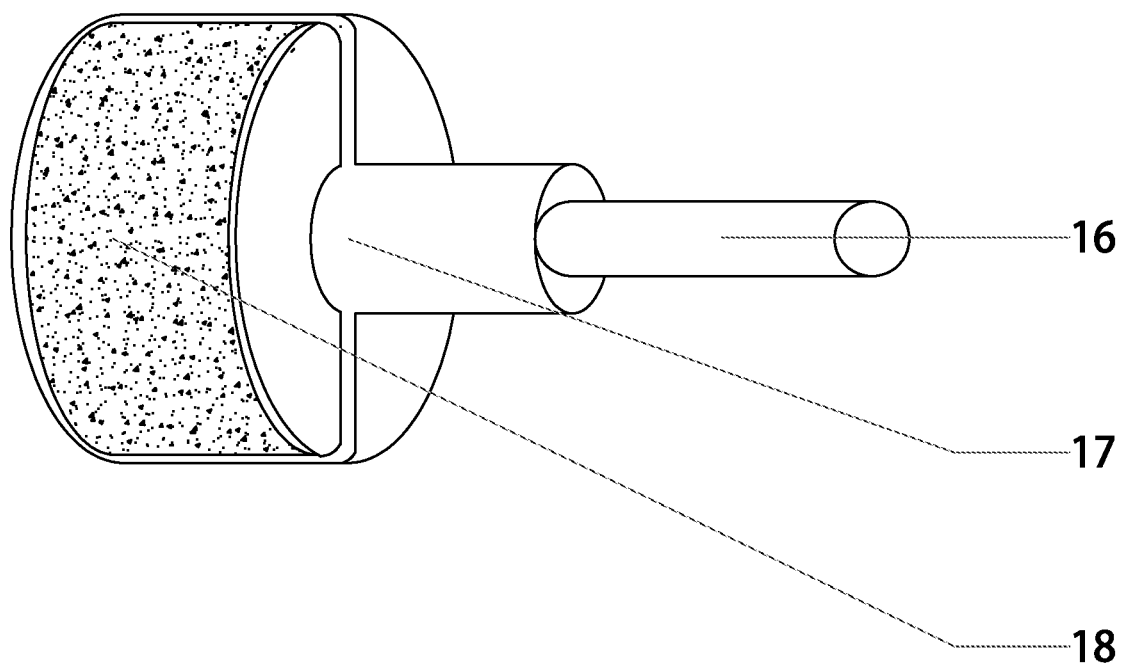
FIG. 7 is a schematic diagram showing connection among the piston, the permeable stone and the metal rod.
Figure 8:
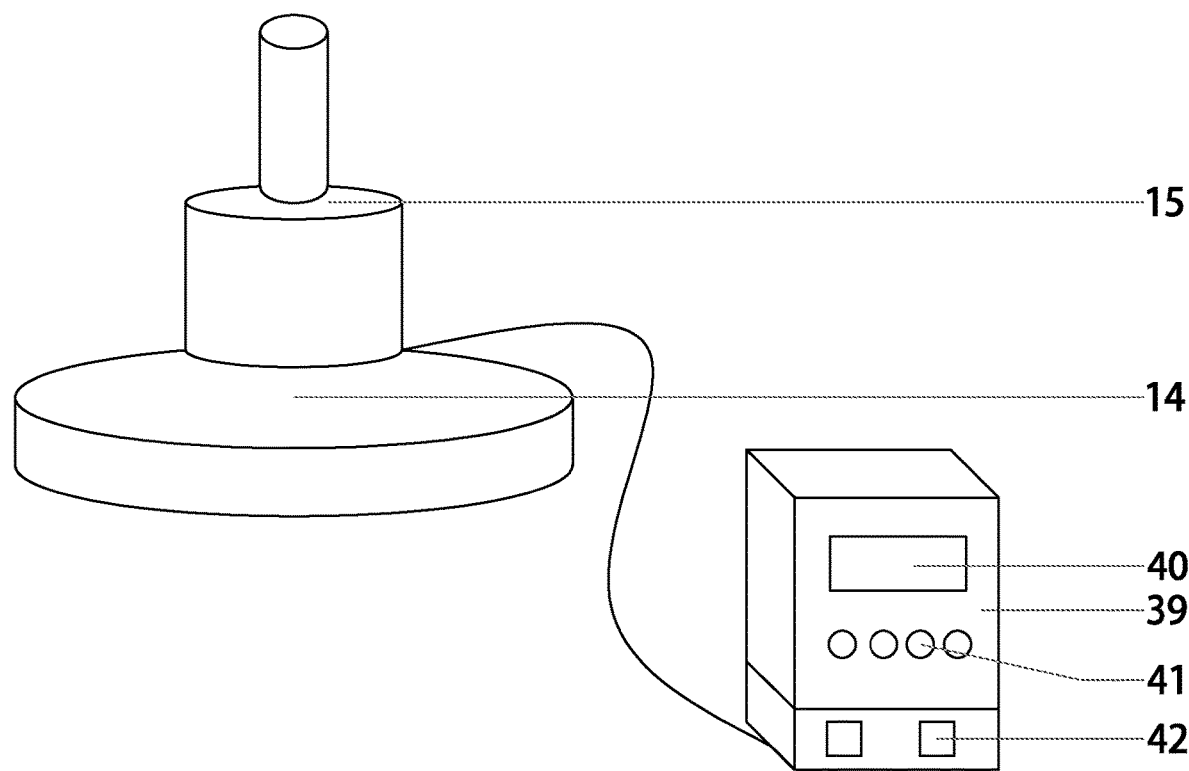
FIG. 8 is a schematic diagram showing connection between the gas cylinder and the intelligent controller.
Figure 9:
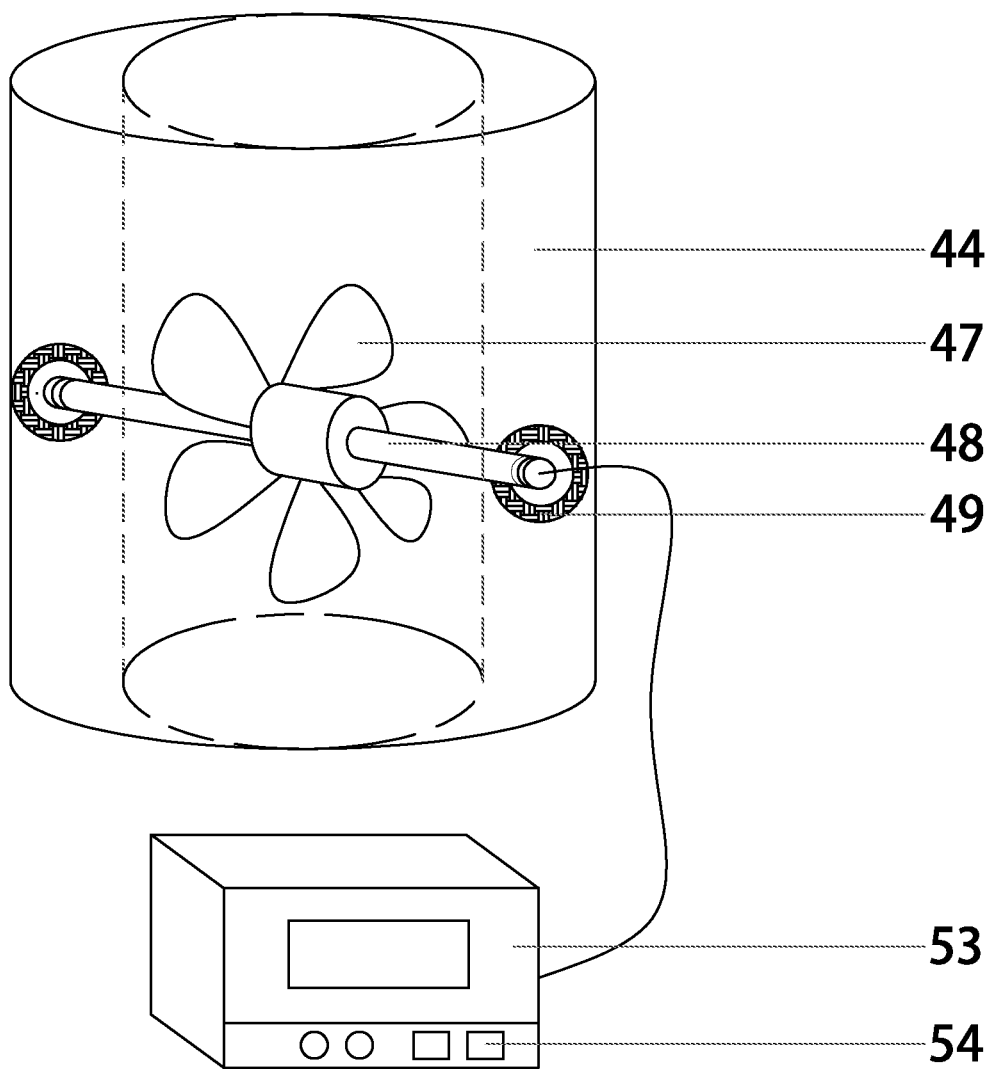
FIG. 9 is a schematic diagram showing connection between the stirring device and the reaction tank.

Embodiment 1: As shown in FIGS. 1-9, a tailings settling-dewatering-solidifying device includes a tailings settling device, a dewatering device, a solidifying device, a stirring system, a dynamic real-time monitoring system and a three-layer framework 25;

the tailings settling device includes a water tank 1, a charging barrel I 10, a charging barrel II 35 and a reaction tank 44 which is made of a transparent material;

the dewatering device includes an intelligent controller 39, a circular base 14, a gas cylinder 15, a permeable stone 18, a piston 17, a metal rod 16 and a water return barrel 50;

the solidifying device includes a charging barrel III 23 and a tailings barrel 52;

the stirring system includes a stirrer 47, a rotary shaft 48 and an electric motor 53;

the dynamic real-time monitoring system includes a high-definition electronic camera 21 and a computer 28;

the charging barrel I 10 and the charging barrel II 35 are placed on a second-layer plate of the three-layer framework 25, and the charging barrel III 23, the reaction tank 44 and the water return barrel 50 are placed on a bottom-layer plate of the three-layer framework 25; a pipeline hole is formed in the framework at each layer; a water inlet 29 is formed in the upper end of the water tank 1 and a water outlet 33 is formed in the lower end of the water tank 1, the left side of the water tank 1 is connected to a water inlet end of a three-phase pipeline joint 6 through a pipeline 5; a horizontal water outlet end of the three-phase pipeline joint 6 is connected to the horizontal end of a right-angled pipeline joint I 4 through a pipeline 5, the vertical water outlet end of the three-phase pipeline joint 6 passes through the uppermost-layer plate of the three-layer framework 25 through the pipeline 5 and then is connected to a charging barrel cap I 9 at the upper end of the charging barrel I 10; the right side of the water tank 1 is connected to the horizontal end of the right-angled pipeline joint II 31 through a pipeline 5, and the vertical end of the right-angled pipeline joint II 31 passes through the uppermost-layer plate of the three-layer framework 25 through a pipeline 5 and then is connected to a charging barrel cap II 34 at the upper end of the charging barrel II 35; the vertical end of the right-angled pipeline joint I 4 sequentially passes through the uppermost-layer plate and the middle-layer plate of the three-layer framework 25 through a pipeline 5 and then is connected to a charging barrel cap III 22 at the upper end of the charging barrel III 23; a control switch I 2 and a flowmeter I 7 are arranged on the pipeline 5 between the water tank 1 and the three-phase pipeline joint 6; a control switch II 3 is arranged on the pipeline 5 between the three-phase pipeline joint 6 and the right-angled pipeline joint 14; a control switch IV 8 is arranged on the pipeline 5 between the three-phase pipeline joint 6 and the charging barrel cap I 9; a control switch III 30 and a flowmeter II 32 are arranged on the pipeline 5 between the water tank 1 and the right-angled pipeline joint II 31; the water outlet end on the bottom of the charging barrel III 23 is connected to one side of the bottom of the reaction tank 44 through a pipeline 5; a control switch VIII 24 is arranged on the pipeline 5 between the charging barrel III 23 and the reaction tank 44; one side of the middle part of the reaction tank 44 is connected to one end of the first water outlet pipeline, and the other end of the first water outlet pipeline extends into the water return barrel 50; a control switch VII 45 is arranged on the first water outlet pipeline; the bottom of the reaction tank 44 is connected to one end of the second water outlet pipeline, and the other end of the second water outlet pipeline extends into the tailings barrel 52, and a control switch IX 51 is arranged on the second water outlet pipeline;

the bottom of one side of the charging barrel I 10 passes through the middle-layer plate of the three-layer framework 25 through a pipeline 5 and then communicates with the upper end of one side of the reaction tank 44; a control switch V 11 and a flowmeter IIII 12 are arranged on the pipeline 5 between the charging barrel I 10 and the reaction tank 44; the bottom of one side of the charging barrel II 35 passes through the middle-layer plate of the three-layer framework 25 through a pipeline 5 and then communicates with the upper end of the other side of the reaction tank 44; a control switch VI 36 and a flowmeter IV 38 are arranged on the pipeline 5 between the charging barrel II 35 and the reaction tank 44; a circular base 14 is fixedly arranged at the lower side of the second-layer plate of the framework 25; the lower end of the circular base 14 is connected to a gas cylinder 15; the gas cylinder 15 is connected to the intelligent controller 39 through an electric wire; the piston 17 is arranged on the top of the rection tank 44; the permeable stone 18 is arranged inside the piston 17; the metal rod 16 is arranged on the upper part of the piston 17; the stirrer 47 is mounted inside the reaction tank 44; a rotary shaft 48 of the stirrer 47 is rotatably connected to the inner wall of the reaction tank 44 through a tube wall interface 49; the rotary shaft 48 is connected to the electric motor 53 through an electric wire; a reversed pipeline hole 19 is formed in the upper-end side wall of the reaction tank 44; and the high-definition electronic camera 21 is mounted on the position opposite to the reaction tank 44 and is connected to the computer 28 through an electric wire.

Further, wheels 27 with brake valves 26 thereon are arranged on the bottom of the three-layer framework 25.

Further, the intelligent controller 39 is fixedly arranged at the front side of the second-layer plate of the three-layer framework 25.

Further, the charging barrel cap I 9 is rotatably connected to the pipeline 5 at the upper end through threads, and the lower part of the charging barrel cap I 9 is rotatably connected to the charging barrel I 10 through threads; the charging barrel I 10 is connected to the pipeline 5 on the bottom through threads; and a connecting way between the charging barrel II 35 and the charging barrel III 23 is the same as the charging barrel I 10.

Further, the piston 17 includes two rubber stoppers with big and small apertures, which are connected through a rubber band; and the diameters of the permeable stone 18 and the metal rod 16 are slightly smaller than the apertures of the two rubber stoppers of the piston 17.

Further, the water inlet 29 and the water outlet 33 are opened or closed by the rubber stoppers.

Further, a display control screen 40, a mode selecting key 41 and a switch button 42 are arranged on the intelligent controller 39.

Further, the circular base 14 is fixed to the lower side of the second-layer plate of the framework 25 through a screw 55, and the circular base 14 is welded and fused with the gas cylinder 15 through metal; and the intelligent controller 39 is fixed at the front side of the second-layer plate of the framework 25 through an electric adhesive tape.

An experimental method of the tailings settling-dewatering-solidifying device includes the following steps:

The experiment aims to perform settling of low-concentration fine-grained tailings slurry after two flocculants are mixed, dewatering after settling and tailings solidifying after dewatering. before the experiment, filling a flocculant a and a flocculant b into the charging barrel I 10 and the charging barrel II 35, injecting low-concentration fine-grained tailings slurry into the reaction tank 44 through the reserved pipeline hole 19, and filling a solidifying agent into the charging barrel III 23;

when the experiment starts, opening the water inlet 29 and closing the water outlet 33 to fill up the water tank 1 with water, opening the control switch I 2, the control switch III 30 and the control switch IV 8 while closing the control switch II 3, the control switch V 11 and the control switch VI 36, controlling the water flow rate by adjusting the opening and closing degree of the control switch I 2 and the control switch III 30, monitoring the water flow rate by the flowmeter I 7 and the flowmeter II 32, making water flow into the charging barrel I 10 and the charging barrel II 35 through corresponding pipelines 5, mixing the water flow with different flow rates with the flocculants a and b to obtain different flocculant concentrations; after obtaining the water flow needed for the experiment, closing the control switch I 2, the control switch IV 8 and the control switch III 30 until the water flows into the corresponding charging barrels;

after mixing the water with the flocculants a and b in the charging barrel I 10 and the charging barrel II 35 for about 2 minutes, opening the control switch V 11, controlling the flow rate of the flocculant a by adjusting the opening and closing degree of the control switch V 11, monitoring the flow rate of the flocculant a by the flowmeter III 12, and closing the control switch V 11 after the flocculant a with a set flow rate flows into the reaction tank 44; switching on an electric motor switch 54 of the electric motor 53, making the stirrer 47 start working, switching off the electric motor switch 54 of the electric motor 53 after stirring for 10 minutes, and making the stirrer 47 stop working; switching on the control switch VI 36, controlling the flow rate of the flocculant b by adjusting the opening and closing degree of the control switch VI 36, monitoring the flow rate of the flocculant b by the flowmeter IV 38, and switching off the control switch VI 36 after the flocculant with the set flow rate flows into the reaction tank 44; making the flocculants a and b have settling reaction with low-concentration fine-grained tailings slurry in the reaction tank 44, photographing a reaction process through the high-definition electronic camera 21, transmitting pictures into the computer 28 for data processing, and basically accomplishing the settling reaction while the data not changed anymore;

after settling reaction is completed, making the experiment enter a dewatering process: electrifying the intelligent controller 39 by an external power supply, switching on the switch button 42 on the intelligent controller 39, making the gas cylinder 15 start working, pushing the metal rod 16 to move downwards by the gas cylinder 15, driving the piston 17 to move downwards by the metal rod 16, separating water from the tailings by the permeable stone 18 mounted in the piston 17 in a downward moving process, switching off the switch button 42 of the intelligent controller 39 while the piston 17 moves to the lower side of the control switch VII 45, making the gas cylinder 15 stop working, standing for certain time, switching on the control switch VII 45 while the water level on the upper part of the permeable stone does not rise again, making upper water flow into the water return barrel 50 through the pipeline 5, switching off the control switch VII 45 after water is completely drained, holding the metal rod 16 with hands, lifting the piston to the top of the reaction tank 44 until the dewatering process is basically accomplished;

and after the dewatering process is accomplished, entering a solidifying reaction stage: switching on the control switch I 2 and the control switch II 3, switching off the control switch IV 8, controlling the water flow rate by adjusting the opening and closing degree of the control switch I 2, monitoring in real time by the flow rate meter I 7, making certain amount of water flow into the charging barrel III 23 through the pipeline 5, mixing the water with a solidifying agent in the charging barrel III 23, switching on the control switch VIII 24, making the solidifying agent with certain concentration flow into the reaction tank 44, and switching off the control switch VIII 24 after mixing the solidifying agent with the dewatered fine-grained tailings slurry; switching on the electric motor switch 54 of the electric motor 53, making the stirrer 47 start working, switching off the electric motor switch 54 of the electric motor 53 after stirring for 3 hours (the specific time depending on specific experimental requirements), and making the stirrer 47 stop working; and switching on the control switch IX 51, and making the solidified tailings flow into a tailings barrel 52 until the whole experiment is accomplished.

The diameters of all pipelines in the embodiment are the same.

The concentrations of the flocculants a and b in the experiment, the concentration of the solidifying agent, impulsive force of the gas cylinder, stirring rotation speed and the like are variables; and the relevant variables are controlled by adjusting the water flow rate, and the rotation speed of the mode selecting key 41 in the intelligent controller 39 and the stirrer 47 to obtain the experimental results.

The above has specifically described the embodiment of the invention in combination with the drawings, but the present invention is not limited to the embodiment. Within the scope of the invention, different variations can be made by one of ordinary skill in the art without departing from the spirit of the present invention.

What is claimed is:

1. A tailings settling-dewatering-solidifying device, comprising a tailings settling device, a dewatering device, a solidifying device, a stirring system, a dynamic real-time monitoring system and a three-layer framework (25);
   wherein the tailings settling device comprises a water tank (1), a charging barrel I (10), a charging barrel II (35) and a reaction tank (44) which is made of a transparent material;
   the dewatering device comprises an intelligent controller (39), a circular base (14), a gas cylinder (15), a permeable stone (18), a piston (17), a metal rod (16) and a water return barrel (50);
   the solidifying device comprises a charging barrel III (23) and a tailings barrel (52);
   the stirring system comprises a stirrer (47), a rotary shaft (48) and an electric motor (53);
   the dynamic real-time monitoring system comprises an electronic camera (21) and a computer (28);
   the charging barrel I (10) and the charging barrel II (35) are placed on a middle-layer plate of the three-layer framework (25), and the charging barrel III (23), the reaction tank (44) and the water return barrel (50) are placed on a bottom-layer plate of the three-layer framework (25); a pipeline hole is formed in the framework at each layer; a water inlet (29) is formed in the upper end of the water tank (1) and a water outlet (33) is formed in the lower end of the water tank (1), the left side of the water tank (1) is connected to a water inlet end of a three-phase pipeline joint (6) through a pipeline (5); a horizontal water outlet end of the three-phase pipeline joint (6) is connected to the horizontal end of a right-angled pipeline joint I (4) through a pipeline (5), the vertical water outlet end of the three-phase pipeline joint (6) connects to a charging barrel cap I (9) at the upper end of the charging barrel I (10), by a pipeline (5) passing through an uppermost-layer plate of the three-layer framework (25); the right side of the water tank (1) is connected to the horizontal end of a right-angled pipeline joint II (31) through a pipeline (5), and the vertical end of the right-angled pipeline joint II (31) connects to a charging barrel cap II (34) at the upper end of the charging barrel II (35), by a pipeline (5) passing through the uppermost-layer plate of the three-layer framework (25); the vertical end of the right-angled pipeline joint I (4) connects to a charging barrel cap III (22) at the upper end of the charging barrel III (23), by a pipeline (5) sequentially passing through the uppermost-layer plate and the middle-layer plate of the three-layer framework (25); a control switch I (2) and a flowmeter I (7) are arranged on the pipeline (5) between the water tank (1) and the three-phase pipeline joint (6); a control switch II (3) is arranged on the pipeline (5) between the three-phase pipeline joint (6) and the right-angled pipeline joint I (4); a control switch IV (8) is arranged on the pipeline (5) between the three-phase pipeline joint (6) and the charging barrel cap I (9); a control switch III (30) and a flowmeter II (32) are arranged on the pipeline (5) between the water tank (1) and the right-angled pipeline joint II (31); the water outlet end on the bottom of the charging barrel III (23) is connected to one side of the bottom of the reaction tank (44) through a pipeline (5); a control switch VIII (24) is arranged on the pipeline (5) between the charging barrel III (23) and the reaction tank (44); one side of the middle part of the reaction tank (44) is connected to one end of a first water outlet pipeline, and the other end of the first water outlet pipeline extends into the water return barrel (50); a control switch VII (45) is arranged on the first water outlet pipeline; the bottom of the reaction tank (44) is connected to one end of a second water outlet pipeline, and the other end of the second water outlet pipeline extends into the tailings barrel (52), and a control switch IX (51) is arranged on the second water outlet pipeline;

the bottom of one side of the charging barrel I (10) communicates with the upper end of one side of the reaction tank (44), by a pipeline (5) passing through the middle-layer plate of the three-layer framework (25); a control switch V (11) and a flowmeter III (12) are arranged on the pipeline (5) between the charging barrel I (10) and the reaction tank (44); the bottom of one side of the charging barrel II (35) communicates with the upper end of the other side of the reaction tank (44), by a pipeline (5) passing through the middle layer plate of the three-layer framework (25); a control switch VI (36) and a flowmeter IV (38) are arranged on the pipeline (5) between the charging barrel II (35) and the reaction tank (44); a circular base (14) is fixedly arranged at the lower side of the middle-layer plate of the three-layer framework (25); the lower end of the circular base (14) is connected to a gas cylinder (15); the gas cylinder (15) is connected to the intelligent type controller (39) through an electric wire; the piston (17) is arranged on the top of the reaction tank (44); the permeable stone (18) is arranged inside the piston (17); the metal rod (16) is arranged on the upper part of the piston (17); the stirrer (47) is mounted inside the reaction tank (44); a rotary shaft (48) of the stirrer (47) is rotatably connected to the inner wall of the reaction tank (44) through a tube wall interface (49); the rotary shaft (48) is connected to the electric motor (53) through an electric wire; a reversed pipeline hole (19) is formed in the upper-end side wall of the reaction tank (44); and the electronic camera (21) is mounted on the position opposite to the reaction tank (44) and is connected to the computer (28) through an electric wire.

2. The tailings settling-dewatering-solidifying device according to claim 1, wherein wheels (27) with brake valves (26) thereon are arranged on the bottom of the three-layer framework (25).

3. The tailings settling-dewatering-solidifying device according to claim 1, wherein the intelligent type controller (39) is fixedly arranged at the front side of the middle-layer plate of the three-layer framework (25).

4. The tailings settling-dewatering-solidifying device according to claim 1, wherein the charging barrel cap I (9) is rotatably connected to the pipeline (5) at the upper end through threads, and the lower part of the charging barrel cap I (9) is rotatably connected to the charging barrel I (10) through threads; the charging barrel I (10) is connected to the pipeline (5) on the bottom through threads; and a connecting way between the charging barrel II (35) and the charging barrel III (23) is the same with that between the charging barrel II (35) and the charging barrel I (10).

5. The tailings settling-dewatering-solidifying device according to claim 1, wherein the piston (17) comprises two rubber stoppers with big and small apertures, which are connected through a rubber band; and the diameters of the permeable stone (18) and the metal rod (16) are slightly smaller than the apertures of the two rubber stoppers of the piston (17).

6. The tailings settling-dewatering-solidifying device according to claim 1, wherein the water inlet (29) and the water outlet (33) are opened or closed by rubber stoppers.

7. The tailings settling-dewatering-solidifying device according to claim 1, wherein a display control screen (40), a mode selecting key (41) and a switch button (42) are arranged on the intelligent type controller (39).

8. The tailings settling-dewatering-solidifying device according to claim 1, wherein the circular base (14) is fixed to the lower side of the middle-layer plate of the three-layer framework (25) through a screw (55), and the circular base (14) is fused with the gas cylinder (15) by metal welding; and the intelligent type controller (39) is fixed at the front side of the middle-layer plate of the three-layer framework (25) by using an electric adhesive tape.

9. An experimental method of the tailings settling-dewatering-solidifying device according to claim 1, comprising the following steps:

before the experiment, filling a flocculant a and a flocculant b into the charging barrel I (10) and the charging barrel II (35), injecting low-concentration fine-grained tailings slurry into the reaction tank (44) through the reserved pipeline hole (19), and filling a solidifying agent into the charging barrel III (23);

when the experiment starts, opening the water inlet (29) and closing the water outlet (33) to fill up the water tank (1) with water, opening the control switch I (2), the control switch III (30) and the control switch IV (8) while closing the control switch II (3), the control switch V (11) and the control switch VI (36), controlling the water flow rate by adjusting the opening and closing degree of the control switch I (2) and the control switch III (30), monitoring the water flow rate by the flowmeter I (7) and the flowmeter II (32), making water flow into the charging barrel I (10) and the charging barrel II (35) through corresponding pipelines (5), mixing the water flow with different flow rates with the flocculants a and b to obtain different flocculant concentrations; after obtaining the water flow needed for the experiment, closing the control switch I (2), the control switch IV (8) and the control switch III (30) until the water flows into the corresponding charging barrelss;

after mixing the water with the flocculants a and b in the charging barrel I (10) and the charging barrel II (35), opening the control switch V (11), controlling the flow rate of the flocculant a by adjusting the opening and closing degree of the control switch V (11), monitoring the flow rate of the flocculant a by the flowmeter III (12), and closing the control switch V (11) after the flocculant a with a set flow rate flows into the reaction tank (44); switching on an electric motor switch (54) of the electric motor (53), making the stirrer (47) start working, switching off the electric motor switch (54) of the electric motor (53) after stirring for 10 minutes, and making the stirrer (47) stop working; switching on the control switch VI (36), controlling the flow rate of the flocculant b by adjusting the opening and closing degree of the control switch VI (36), monitoring the flow rate of the flocculant b by the flowmeter IV (38), and switching off the control switch VI (36) after the flocculant with the set flow rate flows into the reaction tank (44); making the flocculants a and b have settling reaction with low-concentration fine-grained tailings slurry in the reaction tank (44), photographing a reaction process through the electronic camera (21), transmitting pictures into the computer (28) for data processing, and basically accomplishing the settling reaction while the data not changed anymore;

after settling reaction is completed, making the experiment enter a dewatering process: electrifying the intelligent type controller (39) by an external power supply, switching on the switch button (42) on the intelligent type controller (39), making the gas cylinder (15) start working, pushing the metal rod (16) to move downwards by the gas cylinder (15), driving the piston (17) to move downwards by the metal rod (16), separating water from the tailings by the permeable stone (18) mounted in the piston (17) in a downward moving process, switching off the switch button (42) of the intelligent type controller (39) while the piston (17) moves to the lower side of the control switch VII (45), making the gas cylinder (15) stop working, standing for a certain time, switching on the control switch VII (45) while the water level on the upper part of the permeable stone does not rise again, making upper water flow into the water return barrel (50) through the pipeline (5), switching off the control switch VII (45) after water is completely drained, holding the metal rod (16) with hands, lifting the piston to the top of the reaction tank (44) until the dewatering process is basically accomplished;

after the dewatering process is accomplished, entering a solidifying reaction stage: switching on the control switch I (2) and the control switch II (3), switching off the control switch IV (8), controlling the water flow rate by adjusting the opening and closing degree of the control switch I (2), monitoring in real time by the flow rate meter I (7), making certain amount of water flow into the charging barrel III (23) through the pipeline (5), mixing the water with a solidifying agent in the charging barrel III (23), switching on the control switch VIII (24), making the solidifying agent with certain concentration flow into the reaction tank (44), and switching off the control switch VIII (24) after mixing the solidifying agent with the dewatered fine-grained tailings slurry; switching on the electric motor switch (54) of the electric motor (53), making the stirrer (47) start working, switching off the electric motor switch (54) of the electric motor (53) after stirring for set time, and making the stirrer (47) stop working; and switching on the control switch IX (51), and making the solidified tailings flow into a tailings barrel (52) until the whole experiment is accomplished.

\* \* \* \* \*